(12) United States Patent
Bilodeau et al.

(10) Patent No.: US 6,235,741 B1
(45) Date of Patent: May 22, 2001

(54) ANGIOGENESIS INHIBITORS

(75) Inventors: Mark T. Bilodeau; Randall W. Hungate, both of Lansdale; Richard L. Kendall, Doylestown; Ruth Rutledge, Lansdale, all of PA (US); Kenneth A. Thomas, Jr., Chatham, NJ (US); Robert Rubino, Williamsville, NY (US); Mark E. Fraley, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/086,152

(22) Filed: May 28, 1998

Related U.S. Application Data

(60) Provisional application No. 60/048,076, filed on May 30, 1997.

(51) Int. Cl.[7] ............ A61K 31/505; A61K 31/535; C07D 265/30; C07D 403/00
(52) U.S. Cl. ............ 514/257; 514/232.2; 514/231.5; 514/232.8; 514/273; 544/106; 544/117; 544/245; 544/253
(58) Field of Search ............ 544/281, 117, 544/245, 253, 106; 514/233.2, 254, 258, 257, 273, 231.2, 231.5, 232.8

(56) References Cited

U.S. PATENT DOCUMENTS

| | | | |
|---|---|---|---|
| 3,920,652 | * 11/1975 | Springer et al. | 260/256.4 |
| 5,356,897 | * 10/1994 | Oku et al. | 514/258 |
| 5,593,997 | 1/1997 | Dow et al. | 514/258 |

FOREIGN PATENT DOCUMENTS

| | | |
|---|---|---|
| 0 795 555 A1 | 9/1997 | (EP). |
| WO 97/02266 | 1/1997 | (WO). |
| 9729109 | * 8/1997 | (WO). |

OTHER PUBLICATIONS

Database CAPLUS on STN, Chemical Abstract, vol. 124, No. 175795, Selleri et al., "New 2,3–substituted 4,7–dihydro–6–(1H–pyrazolo–3–yl)pyrazolo[1,5a]pyrimidin–7–ones and related compounds: Synthesis and benzodiazepine receptor binding study," abstract, Fa, 1995.*

Sinkula, "Prodrug Approach in Drug Design," Medicinal Chemistry, 1975, vol. 10, pp. 306–315, 1975.*

Burke, "Protein–Tyrosine Kinases: Potential Targets for Anticancer Drug Development," STEM CELLS, vol. 12, pp. 1–6, 1994.*

Bellec et al., "Deaminative electrochemical reduction of pyrazolo[1,5–1]pyrimidine–7–amines," vol. 59, No. 19, pp. 2826–2832, 1981.*

Goldenberg, "Etanercept, a novel drug for the treatment of patients with severe, active rheumatoid arthritis," Clin. Ther., vol. 21, No. 1, pp. 75–87, Jan. 1999.* de Kozak et al., "Tumor necrosis factor and nitric oxide production by resident retinal glial cells from rats presenting hereditary retinal degeneration," vol. 5, No. 2, pp. 85–94, Jun. 1997.*

Spranger et al., "TNF–alpha level in the vitreous body. Increase in neovascular eye diseases and proliferative diabetic retinopathy," Med. Klin., vol. 90, No. 3, pp. 134–137, Mar. 1, 1995.*

Pang et al., "TNF–alpha induction of A1 expression in human cancer cells," vol. 9, No. 11–12, pp. 623–627, 1997.*

Limb et al., "Distribution of TNF alpha and its reactive vascular adhesion molecules in fibrovascular membranes of proliferative diabetic retinopathy," vol. 80, No. 2, pp. 168–173, Feb. 1996.*

Kiyokawa et al., Database HCAPLUS on STN and 1995:315545.

Oku et., Databased HCAPLUS on STAN AN 1993:603440.

Allen et al, Databased HCAPLUS on STAN AN 1992:551008.

Inoue et al., Databased HCAPLUS on STAN AN 1996:181559.

Inoue et al., Databased HCAPLUS on STAN AN 1993:213102.

Inoue et al., Databased HCAPLUS on STAN AN 1992:6580.

M. Shibuya et al., *Onogene*; 5; pp 519–524 (1990).

B. I. Terman Et. Al., *Onogene*; 6(6); pp 1677–1683 (1991).

J. of Med. Chem., vol. 20, No. 3, pp. 386–393 (1977), by W. E. Kirkpatrick, et al.

* cited by examiner

Primary Examiner—Mukund J. Shah
Assistant Examiner—Sudhaker B. Patel
(74) Attorney, Agent, or Firm—J. Antonio Garcia-Rivas; Mark R. Daniel

(57) ABSTRACT

The present invention relates to compounds which inhibit tyrosine kinase enzymes, compositions which contain tyrosine kinase inhibiting compounds and methods of using tyrosine kinase inhibitors to treat tyrosine kinase-dependent diseases/conditions such as angiogenenesis, cancer, atherosclerosis, diabetic retinopathy or autoimmune diseases, in mammals.

3 Claims, No Drawings

ANGIOGENESIS INHIBITORS

RELATED APPLICATIONS

This application claims priority from U.S. Provisional Application No. 60/048,076, filed May 30, 1997.

BACKGROUND OF THE INVENTION

The present invention relates to compounds which inhibit tyrosine kinase enzymes, compositions which contain tyrosine kinase inhibiting compounds and methods of using tyrosine kinase inhibitors to treat tyrosine kinase-dependent diseases/conditions such as neoangiogenesis, cancer, atherosclerosis, diabetic retinopathy or inflammatory diseases, in mammals.

Tyrosine kinases are a class of enzymes that catalyze the transfer of the terminal phosphate of adenosine triphospate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation. Accordingly, inhibitors of these tyrosine kinases are useful for the prevention and treatment chemotherapy of proliferative diseases dependent on these enzymes.

For example, a method of treatment described herein relates to neoangiogenesis. Neoangiogenesis occurs in conjunction with tumor growth and in certain diseases of the eye. It is characterized by excessive activity of vascular endothelial growth factor.

Vascular endothelial growth factor (VEGF) binds the high affinity membrane-spanning tyrosine kinase receptors KDR and Flt-1. Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity.

Vascular growth in the retina leads to visual degeneration culminating in blindness. VEGF accounts for most of the angiogenic activity produced in or near the retina in diabetic retinopathy. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells. Viral expression of a VEGF-binding construct of Flk-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. inhibition of KDR or Flt-1 is implicated in pathological neoangiogenesis, and these are useful in the treatment of diseases in which neoangiogenesis is part of the overall pathology, e.g., diabetic retinal vascularization, as well as various forms of cancer.

Cancers which are treatable in accordance with the present invention demonstrate high levels of gene and protein expression. Examples of such cancers include cancers of the brain, genitourinary tract, lymphatic system, stomach, larynx and lung. These include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma.

SUMMARY OF THE INVENTION

A compound is disclosed in accordance with formula I:

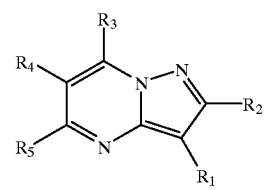

or a pharmaceutically acceptable salt, hydrate or prodrug thereof, wherein $R_1$ is H, $C_{1-10}$ alkyl, $C_{3-6}$ cycloalkyl, $C_{5-10}$ aryl, halo, OH, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;

$R_2$&$R_3$ are independently H, $C_{1-6}$ alkyl, $C_{5-10}$ aryl, $C_{3-6}$ cycloalkyl, OH, $NO_2$, —$NH_2$, or halogen;

$R_4$ is H, $C_{1-10}$ alkyl, $C_{3-6}$ cycloalkyl, $C_{1-6}$ alkoxy $C_{2-10}$ alkenyl, $C_{2-10}$ alkynyl, $C_{5-10}$ aryl, $C_{3-10}$ heterocyclyl, $C_{1-6}$ alkoxy$NR_7R_8$, $NO_2$, OH, —$NH_2$ or $C_{5-10}$ heteroaryl, said alkyl, alkenyl, alkynyl, aryl, heteroaryl and heterocyclyl being optionally substituted with from one to three members selected from $R^a$;

$R_5$ is H, or $C_{1-6}$ alkyl, OR, halo, $NH_2$ or $NO_2$;

$R^a$ is H, $C_{1-10}$ alkyl, halogen, $NO_2$, OR, —NR, $NR_7R_8$, $R_7R_8$, $C_{5-10}$ aryl, $C_{5-10}$ heteroaryl or $C_{3-10}$ heterocyclyl, R is H, or $C_{1-6}$ alkyl; and $R_7$&$R_8$ are independently H, $C_{1-10}$ alkyl, $C_{3-6}$ cycloalkyl, COR, COOR, COO—, $C_{5-10}$ aryl, $C_{3-10}$ heterocyclyl, or $C_{5-10}$ heteroaryl or $NR_7R_8$ can be taken together to form a heterocyclic 5–10 membered saturated or unsaturated ring containing, in addition to the nitrogen atom, one to two additional heteroatoms selected from the group consisting of N, O and S.

Also disclosed is a pharmaceutical composition which is comprised of a compound represented by the formula I:

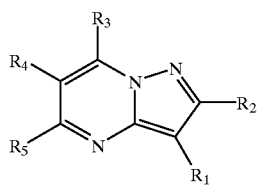

I

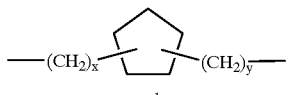

and

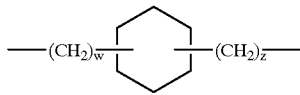

wherein $R_1$, $R_2$, $R_3$, $R_4$ and $R_5$ are described as above or a pharmaceutically acceptable salt or hydrate or prodrug thereof in combination with a carrier.

Also included is a method of treating a tyrosine kinase dependent disease or condition in a mammal which comprises administering to a mammalian patient in need of such treatment a tyrosine kinase dependent disease or condition treating amount of a compound of formula I or a pharmaceutically acceptable salt, hydrate or pro-drug thereof.

Also included is a method of treating cancer in a mammalian patient in need of such treatment which is comprised of admininstering to said patient an anti-cancer effective amount of a compound of formula I or a pharmaceutically acceptable salt, hydrate or pro-drug thereof.

Also included in the present invention is a method of treating diseases in which neoangiogenesis is implicated, which is comprised of administering to a mammalian patient in need of such treatment a compound of formula I or a pharmaceutically acceptable salt, hydrate or pro-drug thereof in an amount which is effective for reducing neoangiogenesis.

More particularly, a method of treating ocular disease in which neoangiogenesis occurs is included herein, which is comprised of administering to a mammalian patient in need of such treatment a compound of formula I or a pharmaceutically acceptable salt hydrate or pro-drug thereof in an amount which is effective for treating said ocular disease.

More particularly, a method of treating retinal vascularization is included herein, which is comprised of administering to a mammalian patient in need of such treatment a compound of formula I or a pharmaceutically acceptable salt, hydrate or pro-drug thereof in an amount which is effective for-treating retinal vascularization. Diabetic retinopathy is an example of a disease in which neoangiogenesis or retinal vascularization is part of the overall disease etiology. Also included is a method of treating age-related macular degeneration.

These and other aspects of the invention will be apparent from the teachings contained herein.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopropyl, cyclobutyl, cycloheptyl, cyclopentyl and cyclohexyl.

Alkyl also includes a straight or branched alkyl group which contains or is interrupted by a cycloalkylene portion. Examples include the following:

wherein: x plus y=from 0–10; and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups of $R^a$, described herein.

The term "alkenyl" refers to a hydrocarbon radical straight, branched or cyclic containing from 2 to 10 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted with one to three groups of $R^a$, when a substituted alkenyl group is provided.

The term "alkynyl" refers to a hydrocarbon radical straight, branched or cyclic, containing from 2 to 10 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted with 1–3 groups of $R^a$, when a substituted alkynyl group is provided.

Aryl refers to 6–10 membered aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 1–3 groups of $R^a$ as defined herein. Preferred substituted aryls include phenyl and naphthyl substituted with one or two groups.

The term heterocycle, heteroaryl or heterocyclic, as used herein except where noted, represents a 5- to 7-membered mono- or bicyclic or 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom. The heterocycle, heteroaryl or heterocyclic may be substituted with 1–3 groups of $R^a$. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrinidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl. The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "prodrug" refers to compounds which are drug precursors which, following administration and absorption, release the drug in vivo via some metabolic process. Exemplary prodrugs include acyl amides of the amino compounds of this inventon such as amides of alkanoic($C_{1-6}$)acids, amides of aryl acids (e.g., benzoic acid) and alkane($C_{1-6}$) dioic acids.

Tyrosine kinase dependent diseases or conditions refers to hyperproliferative disorders which are initiated/maintained by aberrant tyrosine kinase enzyme activity. Examples include psoriasis, cancer, immunoregulation (graft rejection), atherosclerosis, rheumatoid arthritis, angiogenesis (e.g. tumor growth, diabetic retinopathy), etc.

The compounds of the present invention are in accordance with formula I:

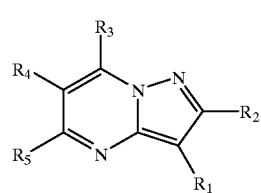

I or a pharmaceutically acceptable salt, hydrate or prodrug thereof,
wherein
$R_1$ is H, $C_{1-10}$ alkyl, $C_{3-6}$cycloallyl, $C_{5-10}$ aryl, halo, OH, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;
$R_2$ & $R_3$ are independently H, $C_{1-6}$ alkyl, $C_{5-10}$ aryl, $C_{3-6}$ cycloalkyl, OH, $NO_2$, —$NH_2$, or halogen;
$R_4$ is H, $C_{1-10}$ alkyl, $C_{3-6}$ cycloalkyl, $C_{3-6}$ alkoxy $C_{2-10}$ alkenyl, $C_{2-10}$ alkynyl, $C_{5-10}$ aryl, $C_{3-10}$ heterocyclyl, $C_{1-6}$ alkoxyNR$_7$R$_8$, $NO_2$, OH, —$NH_2$ or $C_{5-10}$ heteroaryl, said alkyl, alkenyl, alkynyl, aryl, heteroaryl and heterocyclyl being optionally substituted with from one to three members selected from $R^a$;
$R_5$ is H, or $C_{1-6}$ alkyl, OR, halo, $NH_2$ or $NO_2$;
$R^a$ is H, $C_{1-10}$ alkyl, halogen, $NO_2$, OR, —NR, NR$_7$R$_8$, R$_7$R$_8$, $C_{5-10}$ aryl, $C_{5-10}$ heteroaryl or $C_{3-10}$ heterocyclyl,
R is H, or $C_{1-6}$ alkyl; and
$R_7$ & $R_8$ are independently H, $C_{1-10}$ alkyl, $C_{3-6}$ cycloalkyl, COR, COOR, COO—, $C_{5-10}$ aryl, $C_{3-10}$ heterocyclyl, or $C_{5-10}$ heteroaryl or NR$_7$R$_8$ can be taken together to form a heterocyclic 5–10 membered saturated or unsaturated ring containing, in addition to the nitrogen atom, one to two additional heteroatoms selected from the group consisting of N, O and S.

A preferred subset of compounds of the present invention is realized when:
$R_1$ is H, $C_{1-10}$ alkyl, $C_{5-10}$ aryl, $C_{3-10}$ heterocyclyl, or $C_{5-10}$ heteroaryl; said alkyl, aryl, heteroaryl and heterocyclyl being optionally substituted with from one to three members selected from $R^a$;
$R_2$ & $R_3$ are independently H, C alkyl, $C_{3-6}$ cycloalkyl, OH, or halogen;
$R_4$ is H, $C_{1-10}$ alkyl, $C_{3-6}$ cycloalkyl, $C_{5-10}$ aryl, $C_{5-10}$ heteroaryl, $C_{3-10}$ heterocyclyl, $C_{1-6}$ alkoxyNR$_7$R$_8$, $NO_2$, OH, —$NH_2$ or $C_{5-10}$ heteroaryl, said alkyl, aryl, heteroaryl and heterocyclyl being optionally substituted with from one to three members selected from $R^a$; and all other variables are as described above.

Examples of the compounds of this invention are:
3-(4-fluorophenyl)-6-(4-pyridyl) pyrazolo(1,5-A) pyrimidine,
3-(3-chlorophenyl)-6-(4-pyridyl) pyrazolo(1,5-A) pyrimidine,
3-(3,4-methylenedioxypheny)-6-(4-pyridyl) pyrazolo(1,5-A)pyrimidine,
3-(phenyl)-6-(4-pyrimidyl) pyrazolo(1,5-A)pyrimidine,
3-(4-fluorophenyl)-6-(4-pyrimidyl) pyrazolo(1,5-A) pyrimidine,
3-(3-chlorophenyl)-6-(4-pyrimidyl) pyrazolo(1,5-A) pyrimidine,
3-(3-thienyl)-6-(4-pyrimidyl) pyrazolo(1,5-A)pyrimidine,
3-(3-acetamidophenyl)-6-(4-methylphenyl) pyrazolo(1,5-A) pyrimidine,
3-(3-thienyl)-6-(4-methylphenyl) pyrazolo(1,5-A) pyrimidine,
3-(phenyl)-6-(4-methoxyphenyl) pyrazolo(1,5-A) pyrimidine,
3-(3-acetamidophenyl)-6-(4-methoxyphenyl)pyrazolo(1,5-A)pyrimidine,
3-(3-thienyl)-6-(4-methoxyphenyl) pyrazolo(1,5-A) pyrimidine,
3-(phenyl)-6-(4-methoxyphenyl) pyrazolo(1,5-A) pyrimidine,
3-(4-pyridyl)-6-(4-methoxyphenyl) pyrazolo(1,5-A) pyrimidine,
3-(phenyl)-6-(4-chlorophenyl) pyrazolo(1,5-A)pyrimidine.
3-(4-pyridyl)-6-(4-chlorophenyl) pyrazolo(1,5-A) pyrimidine,
3-(phenyl)-6-(4-methylphenyl) pyrazolo(1,5-A)pyrimidine,
3-(4-pyridyl)-6-(4-methylphenyl) pyrazolo(1,5-A) pyrimidine,
3-(phenyl)-6-(2-pyridyl) pyrazolo(1,5-A)pyrimidine,
3-(4-pyridyl)-6-(2-pyridyl) pyrazolo(1,5-A)pyrimidine,
3-(phenyl)-6-(4-pyrimidyl) pyrazolo(1,5-A)pyrimidine,
3-(4-pyridyl)-6-(4-pyrimidyl) pyrazolo(1,5-A)pyrimidine,
3-(phenyl)-6-(2-pyridyl) pyrazolo(1,5-A)pyrimidine,
3-(4-pyridyl)-6-(2-pyrazinyl) pyrazolo(1,5-A)pyrimidine,
3-(3-pyridyl)-6-(4-methoxyphenyl) pyrazolo(1,5-A) pyrimidine,
3-(phenyl)-6-(4-pyridyl) pyrazolo(1,5-A)pyrimidine,
3-(3-pyridyl)-6-(4-pyridyl) pyrazolo(l,5-A)pyrimidine,
3-(4-pyridyl)-6-(4-methoxyphenyl) pyrazolo(1,5-A) pyrimidine,
3-(3-thienyl)-6-(4-methoxyphenyl) pyrazolo(1,5-A) pyrimidine,
3-(3-thienyl)-6-(4-hydroxyphenyl)pyrazolo(1,5-A) pyrimidine,
3-(3-thienyl)-6-(4-(2-(4-morpholinyl)ethoxy)phenyl) pyrazolo(1,5-A)pyrimidine, 3-(3-thienyl)-6-(cyclohexyl)pyrazolo (1,5-A)pyrimidine,
3-(bromo)-6-(4-methoxyphenyl) pyrazolo(1,5-A) pyrimidine,
3-(bromo)-6-(4-pyrimidyl) pyrazolo(1,5-A)pyrimidine,
3-(phenyl)-6-(2-(3-carboxy)pyridyl) pyrazolo(1,5-A) pyrimidine, and
3-(3-thienyl)-6-(4-pyridyl) pyrazolo(1,5-A)pyrimidine.

Schemes 1–3 for preparing the novel compounds of this invention are presented below. The examples which follow the schemes illustrate the compounds that can be synthesized by Schemes 1–3, but Schemes 1–3 are not limited by the compounds in the tables nor by any particular substituents employed in the schemes for illustrative purposes. The examples specifically illustrate the application of the following schemes to specific compounds.

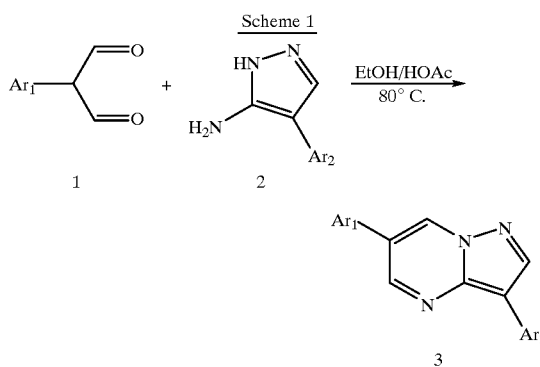

Generally, a method for the preparation of 3,6-diaryl pyrazolo(1,5-A)pyrimidines comprises mixing a commercially available malondialdehyde compound (1), with commercially available aminopyrazole (2) in an alcohol, such as ethanol, methanol, isopropanol, butanol and the like, said alcohol containing catalytic quantities of an acid, such as acetic acid, to yield (3), wherein $A_1$ and $Ar_2$, respectively, are $R_4$ and $R_1$, as described above.

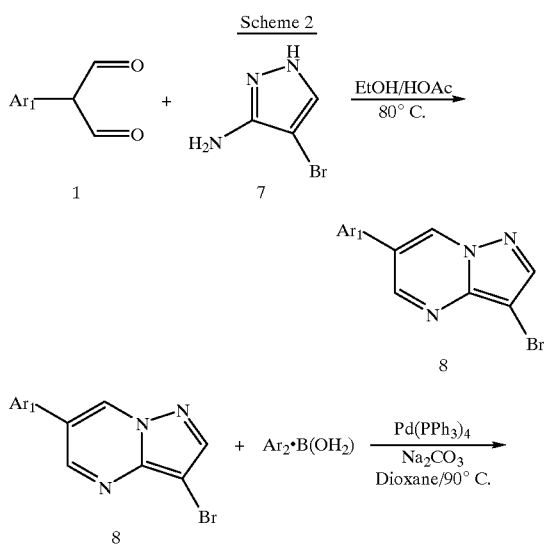

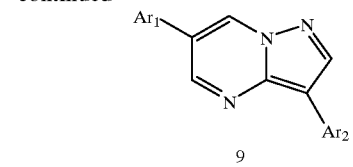

Scheme 2 depicts a means for making 3,6-diaryl pyrazolo (1,5-A)pyrimidines when the desired aminopyrazole is not commercially available. In a like manner to that described in scheme 1 compound (8) is obtained. Treatment of (8) with a boronic acid derivative in the presence of a palladium catalyst provides after workup the desired material (9). $Ar_1$ and $Ar_2$ are as described above.

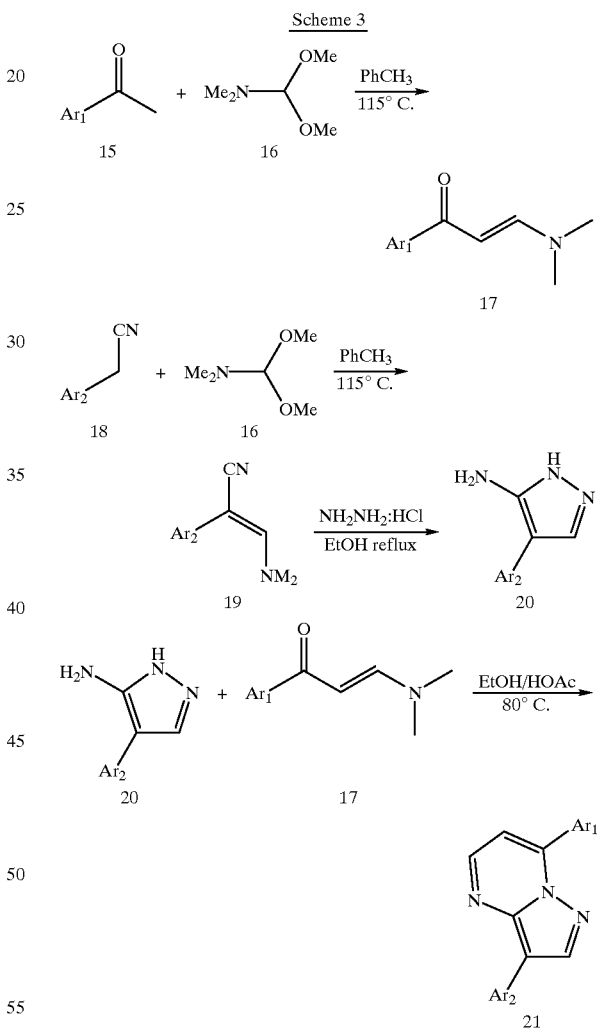

Scheme 3 illustrates another method for the preparation of 3,7 diarylpyrazolo(1,5-A)pyrimidines. The comercially available ketone (15) and nitrile (18) are treated separately with dimethylformamidedimethyl acetal (16) in refluxing toluene to give products (17) and (19) respectively. Compound (19) is then treated with hydrazinehydrochloride in refluxing ethanol to give the aminopyrazole (20). Compounds (17) and (20) and then treated with catalytic amounts of acetic acid in ethanol as described previously giving the desired of 3,7 diarylpyrazolo(1,5-A)pyrimidines (21). $Ar_1$ and $Ar_2$ are as described above.

The invention described herein includes a pharmaceutical composition which is comprised of a compound of formula I or a pharmaceutically acceptable salt or hydrate thereof in combination with a carrier. As used herein the terms "pharmaceutically acceptable salts" and "hydrates" refer to those salts and hydrated forms of the compound which would be apparent to the pharmaceutical chemist, i.e., those which favorably affect the physical or pharmacokinetic properties of the compound, such as solubility, palatability, absorption, distribution, metabolism and excretion. Other factors, more practical in nature, which are also important in the selection, are the cost of the raw materials, case of crystallization, yield, stability, solubility, hygroscopicity and flowability of the resulting bulk drug.

When a compound of formula I is present as a salt or hydrate which is non-pharmaceutically acceptable, this can be converted to a salt or hydrate form which is pharmaceutically acceptable in accordance with the present invention.

When the compound is negatively charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc. An appropriate number of counterions is associated with the molecule to maintain overall charge neutrality. Likewise when the compound is positively charged, e.g., protonated, an appropriate number of negatively charged counterions is present to maintain overall charge neutrality.

Pharmaceutically acceptable salts also include acid addition salts. Thus, the compound can be used in the form of salts derived from inorganic or organic acids or bases. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The compounds of the present invention, may have asymmetric centers and occur as racemates, racemic mixtures and as individual diastereomers, or enantiomers with all isomeric forms being included in the present invention. When any variable (e.g., aryl, heterocyle, R1, etc)occurs more than one time in any constituent or in Formula I, its definition on each occcurence is independent of its definition at every other occurrence, unless otherwise stated.

The compounds of the invention can be formulated in a pharmaceutical composition by combining the compound with a pharmaceutically acceptable carrier. Examples of such compositions and carriers are set forth below.

The compounds may be employed in powder or crystalline form, in solution or in suspension. They may be administered orally, parenterally (intravenously or intramuscularly), topically, transdermally or by inhalation.

Thus, the carrier employed may be, for example, either a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. Similarly, the carrier for oral use may include time delay material well known in the art, such as glyceryl monostearate or glyceryl distearate alone or with a wax.

Topical applications may be formulated in carriers such as hydrophobic or hydrophilic bases to form ointments, creams, lotions, in aqueous, oleaginous or alcoholic liquids to form paints or in dry diluents to form powders. Such topical formulations can be used to treat ocular diseases as well as inflammatory diseases such as rheumatoid arthritis, psoriasis, contact dermatitis, delayed hypersensitivity reactions and the like.

Examples of oral solid dosage forms include tablets, capsules, troches, lozenges and the like. The size of the dosage form will vary widely, but preferably will be from about 25 mg to about 500 mg. Examples of oral liquid dosage forms include solutions, suspensions, syrups, emulsions, soft gelatin capsules and the like. Examples of injectable dosage forms include sterile injectable liquids, e.g., solutions, emulsions and suspensions. Examples of injectable solids would include powders which are reconstituted, dissolved or suspended in a liquid prior to injection.

In injectable compositions, the carrier is typically comprised of sterile water, saline or another injectable liquid, e.g., peanut oil for intramuscular injections. Also, various buffering agents, preservatives and the like can be included.

For the methods of treatment disclosed herein, dosages can be varied depending upon the overall condition of the patient, the nature of the illness being treated and other factors. An example of a suitable oral dosage range is from about 0.1 to about 80 mg/kg per day, in single or divided doses. An example of a suitable parenteral dosage range is from about 0.1 to about 80 mg/kg per day, in single or divided dosages, administered by intravenous or intramuscular injection. An example of a topical dosage range is from about 0.1 mg to about 150 mg, applied externally from about one to four times a day. An example of an inhalation dosage range is from about 0.01 mg/kg to about 1 mg/kg per day.

The compounds may be administered in conventional dosages as a single agent or in combination with other therapeutically active compounds.

EXAMPLE 1

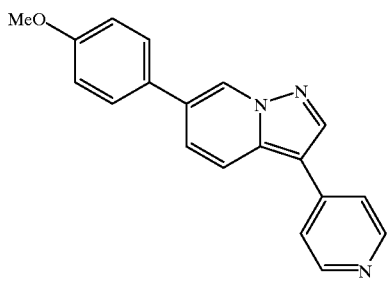

3-(4 pyridyl)-6-(4-methoxyphenyl) pyrazolo(1,5-A) pyrimidine

A solution of commercially available dialdehyde (4, 12.9 mg, 0.0724 mmol) and aminopyrazole (5, 10.4 mg 0.0652 mmol) in ethanol was heated at 80° C. for 10 hours in a test tube containing catalytic amounts of acetic acid. The reaction was cooled to room temperature and the yellow solid was collected by filtration and the title compound was washed with cold ethanol and dried (11.7 mg, 60%). Mass Spec (M+1, 303).

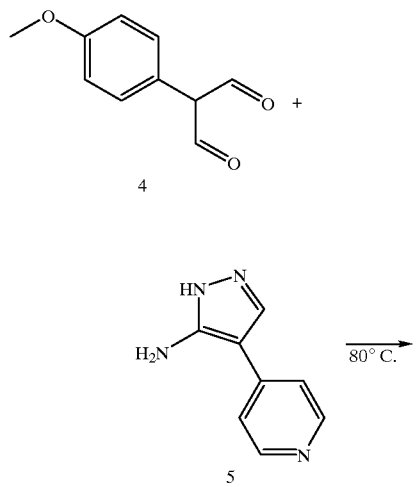

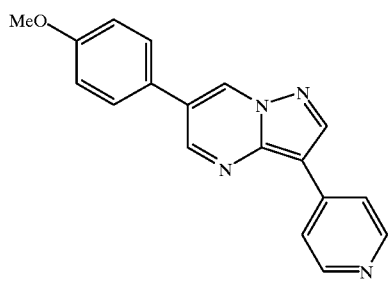

EXAMPLE 2

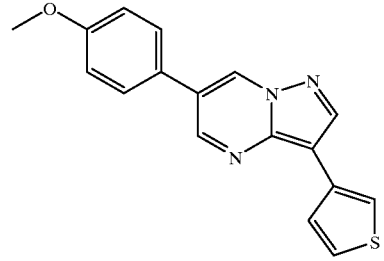

3-(3-thienyl)-6-(4-methoxyphenyl) pyrazolo(1,5-A) pyrimidine

Step 1.

A solution of 4 (713 mg, 4.0 mmol) and commercially availaible 7 (648 mg, 4.0 mmol), discussed above in ethanol (20 mL) was heated at 75° C. for 4 h. The resulting white suspension was as decribed in example 1 for 4 hours, then cooled to 20° C., filtered, and washed with methanol (3×5 mL) to provide 10 as a white powder (1.07 g, 88%, mp =168–170° C.): 1H NMR (CDCl$_3$) δ8.79 (d, 1H, J=2.2Hz), 8.74 (d, 1H, J=2.2Hz), 8.12 (s, 1H), 7.51 (d, 2 H, J=8.8Hz), 7.05 (d, 2 H, J=8.8Hz), 3.88 (s, 3H).

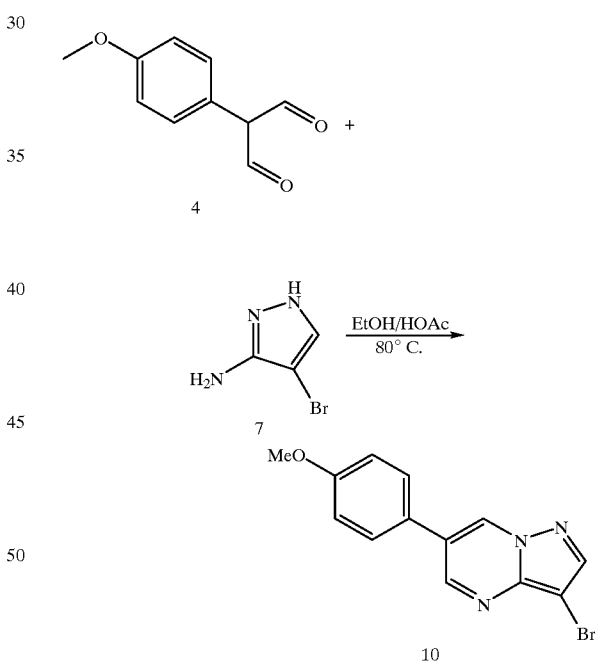

Step 2.

A suspension of (10) (250 mg, 0.82 mmol), thiophene-3-boronic acid (11) (158 mg, 1.24 mmol), and aqueous sodium carbonate (2 M, 1 mL) in dioxane (5 mL) was de-gassed by evacuating and backflushing with argon (3x). Tetrakis (triphenyl-phosphine) palladium (20 mg, 0.017 mmol) was added and the reaction mixture was de-gassed again. The argon filled flask was then submerged in an oil bath pre-heated to 90° C. and was heated at that temperature for 16 h. After cooling to 20° C., the yellow precipitate which formed was collected by filtration and was washed with methanol (3×5 mL) to provide the title compound as a yellow powder (220 mg, 87%, mp=191–193° C.): $^1$H NMR (CDCl$_3$) δ8.79 (d, 1H, J=2.4Hz), 8.76 (d, 1H, J=2.2Hz), 8.37 (s, 1H), 7.90 (dd, 1H, J=2.9, 1.3Hz), 7.70 (dd, 1H, J=4.9, 1.2Hz), 7.54 (d, 2H, J=8.8Hz), 7.43 (d, 1H, J=4.9, 2.9Hz), 7.06 (d, 2H, J=8.8Hz), 3.88 (s, 3H).

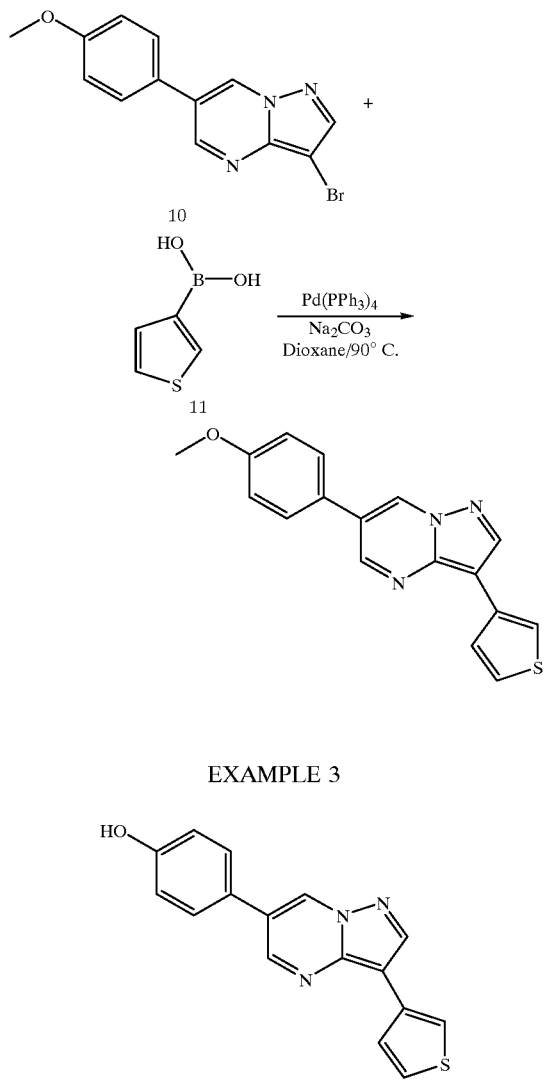

EXAMPLE 3

3-(3-thienyl)-6-(4-hydroxyphenyl)pyrazolo(1,5-A)pyrimidine

Ethanethiol (30 mg, 36 uL) was added dropwise over 1 min to a suspension of sodium hydride (23 mg, 0.98 mmol) in 10 dry DMF (2 mL) under argon. After 15 min, the compound of example 2 (50 mg, 0.16 mmol) was added and the reaction mixture was heated at 150° C. for 1.5 h. The resulting brown solution was cooled, poured into water (25 mL) and washed with ethyl acetate (2×25 mL). The combined organics were dried (Na$_2$SO$_4$), is concentrated, and purified by flash chromatography (40% EtOAc/Hexanes) to give the title compound as a yellow solid [11 mg, 23%, R$_f$=0.12 (40% EtOAc/Hexanes)]: $^1$H NMR (CD$_3$OD) δ8.96 (d, 1H, J=2.4Hz), 8.85 (d, 1H, J=2.2Hz), 8.44 (s, 1H), 7.94 (dd, 1H, J=2.9, 1.2Hz), 7.74 (dd, 1H, J=4.9, 1.2Hz), 7.56 (d, 2 H, J=8.8Hz), 7.46 (dd, 1H, J=4.9, 2.9Hz), 6.94 (d, 2H,J=8.6Hz).

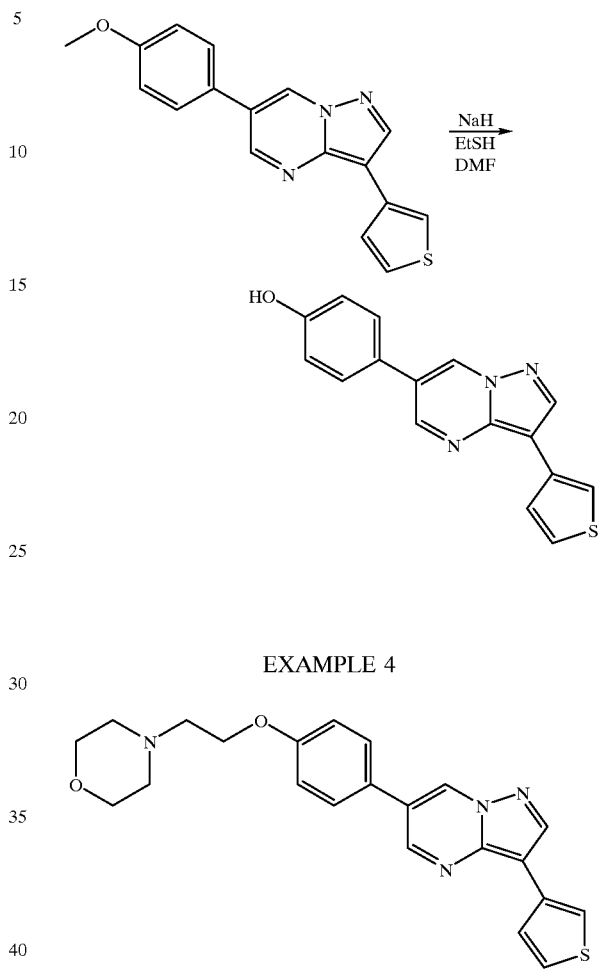

EXAMPLE 4

3-(3-thienyl)-6-(4-(2-(4-morpholinyl)ethoxy)phenyl)pyrazolo(1,5-A)pyrimidine

A solution of example 3 (11 mg, 0.038 mmol), cesium carbonate (37 mg, 0.11 mmol), N-(2-chloroethyl)morpholine hydrochloride (7 mg, 0.11 mmol), and sodium iodide (0.013 mmol) in DMF (3 mL) was heated at 60° C. under argon for 16 h. The reaction mixture was then poured into water (25 mL) and washed with ethyl acetate (2×25 mL). The combined organics were dried (Na$_2$SO$_4$), concentrated, and purified by flash chromatography [50% Hexanes/CHCl$_3$(NH$_3$)] to give the title compound as a yellow solid [10 mg, 65%, mp =149–151° C., R$_f$=0.39 (100% CHCl$_3$(NH$_3$))]: $^1$H NMR (CDCl$_3$) δ8.77 (d, 1H, J=2.2Hz), 8.75 (d, 1H, J=2.2Hz), 8.36 (s, 1H), 7.90 (dd, 1H, J=2.9, 1.3 Hz), 7.69 (dd, 1H, J=4.9, 1.3Hz), 7.52 (d, 2 H, J=8.8Hz), 7.43 (d, 1H, J=4.9, 2.9Hz), 7.06 (d, 2 H, J=8.8Hz), 4.18 (t, 2 H, J=5.7Hz), 3.76 (t, 4 H, J=4.6Hz), 2.85 (t, 2 H, J=5.7 Hz), 2.61 (t, 4 H, J=4.6Hz); FAB MS (M$^+$+1) Anal Calcd. for C$_{22}$H$_{22}$N$_4$O$_2$S : C, 65.00; H, 5.46; N, 13.78. Found C, 64.98; H, 5.55; N, 14.02.

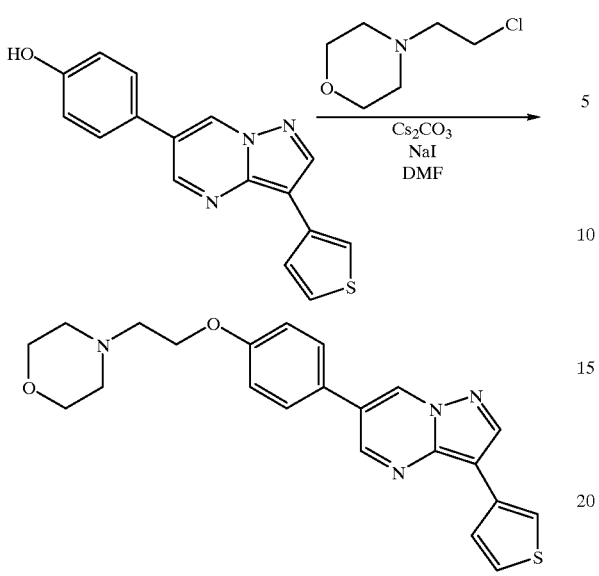

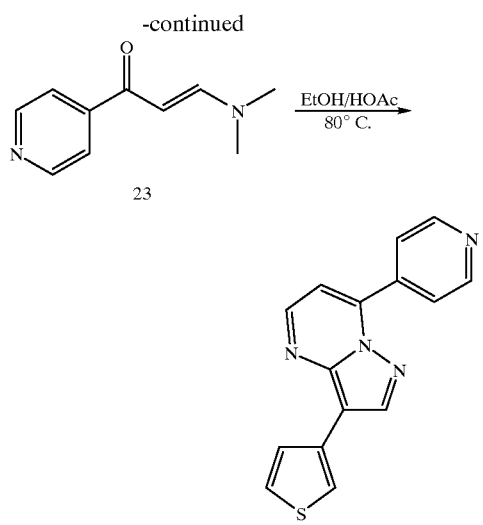

EXAMPLE 5

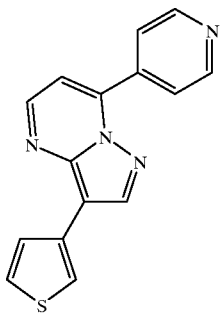

3-(3-thiophenyl)-7-(4-pyridyl) pyrazolo(1,5-A) pyrimidine

A 13×100 mm reaction tube was charged with aminopyrazole (22) (16.5 mg, 0.100 mmol) dissolved in 0.500 mL EtOH and vinylogous amide (23) (17.6 mg, 0.100 mmol) dissolved in 0.200 mL ETOH. Glacial acetic acid (1 drop) was added and the reaction was heated to 80° C. for 14 h. An additional 0.100 mL of glacial acetic acid was added and heating was continued for an additional 6 h. The sample was concentrated to dryness to provide the desired title compound. Analysis by mass spectrometry showed [M+H]$^+$ 279.2.

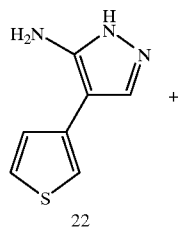

EXAMPLE 6

3-(3-thienyl)-6-(cyclohexyl) pyrazolo(1,5-A) pyrimidine

Step 1

Palladium on carbon (10%, 2 g) was added to a solution of 24 (5.62 g, 23.4 mmol) in ethanol (100 mL) under an argon atmosphere. After evacuating and backflushing the reaction vessel with H$_2$ (3X), the black suspension was stirred vigorously under an H$_2$ filled balloon for 16 h. The reaction mixture was then filtered through celite, washed with ethyl acetate (200 mL) and concentrated to provide 25 as a colorless oil (5.0 g, 88%): $^1$H NMR (CDCl$_3$) d 4.18 (q, 4H, J=7.1Hz), 3.13 (d, 1H, J=9.2 Hz), 2.08 (m, 1H), 1.73–1.56 (m, 5H), 1.35–1.01 (m, 5H), 1.26 (t, 6H, J=7.0Hz).

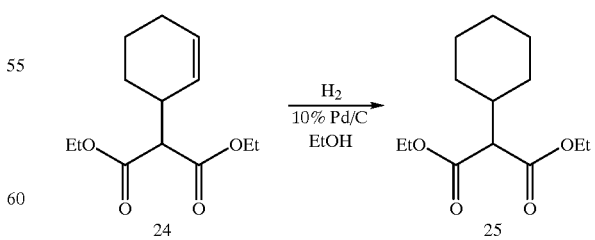

Step 2

A solution of 25 (2.0 g, 8.3 mmol) in dry THF (30 mL) at 0° C. was treated with lithium aluminum hydride (1.0 M in THF, 16.5 mL, 16.5 mmol) over a 5 min period. The reaction mixture was warmed gradually to 15° C. over 20 min and then was re-cooled to 0° C. and quenched sequentially with water (630 uL), aqueous sodium hydroxide (1 N, 630 uL), and then water (3×630 uL). The resulting white suspension was stirred for 15 min, dried (Na$_2$SO$_4$), and filtered washing with THF (100 mL) and ethyl acetate (100 mL). The filtrate was concentrated to provide 26 as a white solid (1.35 g, 100%): $^1$H NMR (CDCl$_3$) d 3.83 (ddd, 4H), 1.77–1.62 (m, 5H), 1.57 (m, 1H), 1.42 (m, 1H), 1.30–0.96 (m, 5H).

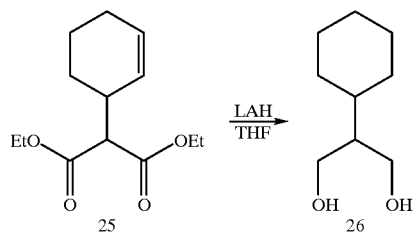

Step 3

A solution of oxalyl chloride (2.39 g, 1.64 mL, 18.8 mmol) in CH$_2$Cl$_2$ (50 mL) at −60° C. was treated with DMSO (2.94 g, 2.67 mL, 37.6 mmol) in CH$_2$Cl$_2$ (10 mL) over 2 min. After 5 min, a solution of 26 (1.35 g, 8.5 mmol) in CH$_2$Cl$_2$ (20 mL) was added and the resulting suspension was maintained at −60° C. for 15 min. Triethylamine (8.6 g, 11.8 mL, 85 mmol) was then added and the reaction mixture was allowed to warm to 20° C. The quenched reaction was poured into water (200 mL) and washed with CH$_2$Cl$_2$ (2×100 mL). The combined organics were dried (Na$_2$SO$_4$), concentrated, and purified by flash chromatography (40% Hexane/EtOAc) to provide 27 as a viscous oil [135 mg, 10%, R$_f$=0.34 (40% Hexane/EtOAc)]: $^1$H NMR (CDCl$_3$) d 8.26 (s, 2H), 2.09 (tt, 1H), 1.85–1.68 (m, 6H), 1.39–1.13 (m, 5H).

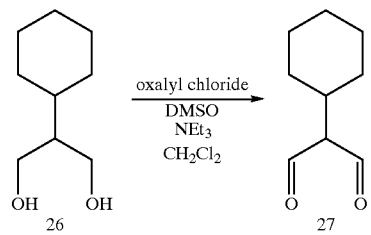

Step 4

A solution of 27 (50 mg, 0.30 mmol) and 22 (47 mg, 0.30 mmol) in ethanol (5 mL) was heated at 75° C. for 16 h. After cooling, the reaction mixture was concentrated, and the crude product was purified by flash chromatography (25% EtOAc/Hexane) to provide 6 as a yellow solid [54 mg, 63%, R$_f$=0.33 (25% EtOAc/Hexanes)]: $^1$H NMR (CDCl$_3$) d 8.48 (d, 1H, J=2.2Hz), 8.44 (d, 1H, J=1.5Hz), 8.30 (s, 1H), 7.86 (dd, 1H, J=2.9, 1.1Hz), 7.66 (dd, 1H, J=4.9, 1.2Hz), 7.41 (dd, 1H, J=4.9, 2.9Hz), 2.64 (m, 1H), 2.03–1.80 (m, 5H), 1.52–1.27 (m, 5H); FAB MS (M$^+$+1) calcd. for 284, found 284; Anal Calcd. for C$_{16}$H17N$_3$S (0.05 H$_2$O): C, 67.59; H, 6.06; N, 14.78. Found C, 67.66; H, 6.12; N, 15.14.

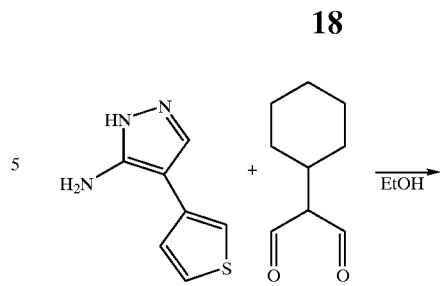

Kinase inhibition is demonstrated in accordance with the following protocol.

VEGF RECEPTOR KINASE ASSAY

VEGF receptor kinase activity is measured by incorporation of radio-labeled phosphate into polyglutamic acid, tyrosine, 4:1 (pEY) substrate. The phosphorylated pEY product is trapped onto a filter membrane and the incoporation of radio-labeled phosphate quantified by scintillation counting.

MATERIALS

VEGF receptor kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis buffer 50 mM Tris pH 7.4, 0.5 M NaCl, 5 mM DTT, 1 mM EDTA, 0.5% triton X-100, 10% glycerol, 10 mg/ml of each leupeptin, pepstatin and aprotinin and 1 mM phenylmethylsulfonyl fluoride (all Sigma).

Wash buffer 50 mM Tris pH 7.4, 0.5 M NaCl, 5 mM DTT, 1 mM EDTA, 0.05% triton X-100, 10% glycerol, 10 mg/ml of each leupeptin, pepstatin and aprotinin and 1 mM phenylmethylsulfonyl fluoride.

Dialysis buffer 50 mM Tris pH 7.4,0.5 M NaCl, 5 mM DTT, 1 mM EDTA, 0.05% triton X-100, 50% glycerol, 10 mg/ml of each leupeptin, pepstatin and aprotinin and 1 mM phenylmethylsuflonyl fluoride 10 X reaction buffer 200 mM Tris, pH 7.4, 1.0 M NaCl, 50 mM MnCl$_2$, 10 mM DTT and 5 mg/ml bovine serum albumin (Sigma).

Enzyme dilution buffer 50 mM Tris, pH 7.4, 0.1 M NaCl, 1 mM DTT, 10% glycerol, 100 mg/ml BSA.

10 X Substrate

750 μg/ml poly (glutamic acid, tyrosine; 4:1) (Sigma).

Stop solution

30% trichloroacetic acid, 0.2 M sodium pyrophosphate (both Fisher).

Wash solution

15% trichloroacetic acid, 0.2 M sodium pyrophosphate.

Filter plates

Millipore #MAFC NOB, GF/C glass fiber 96 well plate.

METHOD

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000 X g and lysed at 4° C. for 30 minutes with 1/10 volume of lysis buffer followed by centrifugation at 100,000Xg for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF receptor kinase assay

1. Add 5 μl of inhibitor or control to the assay in 50% DMSO.

2. Add 35 μl of reaction mix containing 5 μl of 10 X reaction buffer, 5 μl 25 mM ATP/10 1Ci [$^{33}$P]ATP (Amersham), and 5 μL 10 X substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μL aliquot to filter plate.

8. Aspirate and wash 3 times with wash solution.

9. Add 30 μl of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to 1X concentration are made directly into Assay Medium immediately prior to addition to cells.

10X Growth factors

Solutions of human VEGF$_{165}$ (500 ng/ml; R&D Systems) and bFGF (10 ng/ml; R&D Systems) are prepared in Assay Medium.

10X [$^3$H]Thymidine

[Methyl-$^3$H]Thymidine (20 Ci/mmol; Dupont-NEN) is diluted to 80 uCi/ml in low-glucose DMEM.

Cell Wash Medium

Hank's balanced salt solution (Mediatech) containing 1 mg/ml bovine serum albumin (Boehringer-Mannheim).

Cell Lysis Solution

1N NaOH, 2% (w/v) Na$_2$CO$_3$.

Method

1. HUVEC monolayers maintained in EGM are harvested by trypsinization and plated at a density of 4000 cells per 100 ul Assay Medium per well in 96-well plates. Cells are growth-arrested for 24 hours at 37° C in a humidified atmosphere containing 5% CO$_2$.

2. Growth-arrest medium is replaced by 100 ul Assay Medium containing either vehicle (0.25% [v/v] DMSO) or the desired final concentration of test compound. All determinations are performed in triplicate. Cells are then incubated at 37° C./5% CO$_2$ for 2 hours to allow test compounds to enter cells.

3. After the 2-hour pretreatment period, cells are stimulated by addition of 10 ul/well of either Assay Medium, 10X VEGF solution or 10X bFGF solution. Cells are then incubated at 37° C./5% CO$_2$.

4. After 24 hours in the presence of growth factors, 10X [$^3$H]Thymidine (10 ul/well) is added.

5. Three days after addition of [$^3$H]thymidine, medium is removed by aspiration, and cells are washed twice with Cell Wash Medium (400 ul/well followed by 200 ul/well). The washed, adherent cells are then solubilized by addition of Cell Lysis Solution (100 ul/well) and warming to 37° C. for 30 minutes. Cell lysates are transferred to 7-ml glass scintillation vials containing 150 ul of water. Scintillation cocktail (5 ml/vial) is added, and cell-associated radioactivity is determined by liquid scintillation spectroscopy.

Based upon the foregoing assays the compounds of formula I are inhibitors of VEGF and thus are useful for the inhibition of neoangiogenesis, such as in the treatment of occular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 150–650 nM. These compounds also show selectivity over related tyrosine kinases (e.g. FGFRI and the Src family).

What is claimed is:

1. A compound in accordance with formula I:

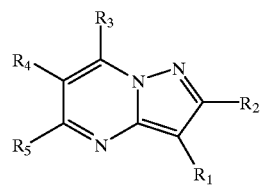

or a pharmaceutically acceptable salt or hydrate thereof, wherein
- $R_1$ is pyridyl, pyrimidyl, thienyl or pyrazinyl, optionally substituted with from one to three members selected from $R^a$;
- $R_2$ is H or $C_{1-6}$ alkyl;
- $R_3$ and $R_4$ are selected from the group consisting of phenyl, pyridyl, pyrimidyl, thienyl or pyrazinyl, optionally substituted with from one to three members selected from $R^a$, provided that only one of $R_3$ and $R_4$ is as defined above and the other is H or $C_{1-6}$ alkyl;
- $R_5$ is H, $C_{1-6}$ alkyl, OR, halo, $NH_2$ or $NO_2$;
- $R^a$ is H, $C_{1-10}$ alkyl, halogen, OH, $OC_{1-6}$ alkyl, $NR_7R_8$ or phenyl, said $OC_{1-6}$ alkyl is optionally substituted with $NR_7R_8$;
- R is H or $C_{1-6}$ alkyl; and
- $R_7$ and $R_8$ are independently selected from: H, $C_{1-10}$ alkyl, $C_{3-6}$ cycloalkyl, COR, COOR, $C_{6-10}$ aryl, and $C_{3-6}$ heterocyclyl, or $R_7$ and $R_8$ can be taken together with the nitrogen to which they are attached to form a heterocyclic 5–10 membered saturated or unsaturated ring containing, in addition to the nitrogen atom, one to two additional heteroatoms selected from the group consisting of N, O and S.

2. A compound in accordance with claim 1 wherein $R_7$ and $R_8$ are independently selected from: H, $C_{1-10}$ alkyl, $C_{3-6}$ cycloalkyl, COR, COOR, $C_{6-10}$ aryl, and $C_{3-6}$ heterocyclyl, or $R_7$ and $R_8$ can be taken together with the nitrogen to which they are attached to form a heterocyclic 5 or 6 membered saturated or unsaturated ring containing, in addition to the nitrogen atom, one to two additional heteroatoms selected from the group consisting of N, O and S.

3. A compound according to claim 1 selected from:
3-(3-thienyl)-6-(4-pyrimidyl) pyrazolo(1,5-A) pyrimidine,
3-(3-thienyl)-6-(4-methylphenyl) pyrazolo(1,5-A) pyrimidine,
3-(3-thienyl)-6-(4-methoxyphenyl) pyrazolo(1,5-A) pyrimidine,
3-(4-pyridyl)-6-(4-methoxyphenyl) pyrazolo(1,5-A) pyrimidine,
3-(4-pyridyl)-6-(4-chlorophenyl) pyrazolo(1,5-A) pyrimidine,
3-(4-pyridyl)-6-(4-methylphenyl) pyrazolo(1,5-A) pyrimidine,
3-(4-pyridyl)-6-(2-pyridyl) pyrazolo(1,5-A)pyrimidine,
3-(4-pyridyl)-6-(4-pyrimidyl) pyrazolo(1,5-A) pyrimidine,
3-(4-pyridyl)-6-(2-pyrazinyl) pyrazolo(1,5-A)pyrimidine,
3-(3-pyridyl)-6-(4-methoxyphenyl) pyrazolo(1,5-A) pyrimidine,
3-(3-pyridyl)-6-(4-pyridyl) pyrazolo(1,5-A)pyrimidine,
3-(4-pyridyl)-6-(4-methoxyphenyl) pyrazolo(1,5-A) pyrimidine,
3-(3-thienyl)-6-(4-hydroxyphenyl)pyrazolo(1,5-A) pyrimidine,
3-(3-thienyl)-6-(4-(2-(4-morpholinyl)ethoxy)phenyl) pyrazolo(1,5-A)pyrimidine,
3-(3-thienyl)-6-(cyclohexyl)pyrazolo (1,5-A)pyrimidine,
3-(3-thienyl)-6-(4-pyridyl) pyrazolo(1,5-A)pyrimidine,
3-(3-thienyl)-7-(4-pyridyl) pyrazolo(1,5-A)pyrimidine, or a pharmaceutically acceptable salt thereof.

* * * * *